United States Patent [19]

Muhler et al.

[11] 4,122,163

[45] Oct. 24, 1978

[54] DENTIFRICE PREPARATION COMPRISING PURIFIED, CALCINED KAOLIN ABRASIVES

[75] Inventors: Joseph C. Muhler, Howe; Mark S. Putt, Ft. Wayne, both of Ind.

[73] Assignee: Indiana University Foundation, Bloomington, Ind.

[21] Appl. No.: 710,444

[22] Filed: Aug. 2, 1976

[51] Int. Cl.$^2$ .............................................. A61K 7/18
[52] U.S. Cl. ..................................................... 424/52
[58] Field of Search .................................. 424/49–58; 51/307–309

[56] References Cited

U.S. PATENT DOCUMENTS

| 906,339 | 12/1908 | Tone | 51/308 |
|---|---|---|---|
| 1,275,275 | 8/1918 | Levinson | 424/49 |
| 2,256,528 | 9/1941 | Rowe et al. | 51/308 |
| 2,441,534 | 5/1948 | Norton | 51/308 |
| 3,105,013 | 9/1963 | Saul et al. | 424/52 |
| 3,282,792 | 11/1966 | Fiscella | 424/52 |
| 3,477,809 | 11/1969 | Bundy et al. | 23/110 |

FOREIGN PATENT DOCUMENTS

| M3,610 | 11/1965 | France. |
|---|---|---|
| 1,273,859 | 2/1962 | France. |
| 7,424,224 | 6/1974 | Japan. |
| 176,091 | 4/1948 | Japan. |

OTHER PUBLICATIONS

Ericsson Chem. Abstr. 59 #7315c (1963) Abstr. of Acta. Odontol, Scand. 20:441-451 (1962) Aluminum Compounds in Fluorinated Toothpastes and Dental Prophylaxis Pastes.
Koren Chem. Abstr. 69 #99376M (1968) Abstr. of Maslozhir Prom (1968) 34(8):31-34 Abrasive Properties of Some Domestic Toothpastes and Powders.
Glenn Chem. Abstr. 33 #2748$^{(7)}$ (1939) Abstr. of Soap, Perfumery & Cosmetics 11:1107-1108 (1939) Colloidal Kaolin in Soaps and Cosmetics.
Hojka Chem. Abstr. 33 #7959$^{(3)}$ (1939) Abstr. of Coskoslov. Mydlar, Vonaukar 16:6-7 (1938) The Uses of Colloidal Kaolins.

*Primary Examiner*—Shep K. Rose
*Attorney, Agent, or Firm*—Kirkland & Ellis

[57] ABSTRACT

New and more effective dentifrice preparations may be obtained by employing therein a cleaning and polishing constitutent comprising purified, calcined kaolin particles. Additionally, anticariogenic adjuvants such as sodium fluoride, NaF, may be incorporated in such dentifrice preparations.

11 Claims, No Drawings

DENTIFRICE PREPARATION COMPRISING PURIFIED, CALCINED KAOLIN ABRASIVES

BACKGROUND OF THE INVENTION

1. Field of the Invention

The present invention relates to new dentifrice cleaning and polishing agents and to the formulation and utilization of dentifrice preparations incorporating such cleaning and polishing agents. In particular, the invention relates to a dentifrice cleaning and polishing composition comprising purified, calcined kaolin particles predominantly of the gamma alumina and/or mullite form, not more than a minor amount of titanium-containing impurities being present and the particles being at least predominantly less than about 10 microns in diameter.

These compositions serve to clean and polish dental hard tissue in a novel manner such that reaccumulations of pellicle and materia alba and occurrence and reformation of calculus on oral hard tissue are markedly reduced, thereby significantly reducing the occurrence of gingivitis and other soft tissue and periodontal disease. Fluoride-containing anticariogenicadjuvants such as sodium fluoride, NaF, may also usefully be incorporated in such compositions.

2. Description of the Prior Art

Dental research has developed substantial evidence that beyond the age of thirty-five years loss of teeth is predominantly the result of periodontal involvement rather than dental caries. However, evidence in the literature suggests that gingivitis itself may be present in a large portion of the population at a much earlier age. In this form the disease is reversible. A major factor contributing to periodontal disease is the accumulation of certain forms of dental plaque and calculus (e.g., salivary tartar) on the teeth. These accumulations result in tissue inflammation of the surrounding gingiva, and, as the condition increases in severity, the periodontal fibers and supporting bone subsequently become affected. These reactions lead to the destruction of the supporting structures and the subsequent mass loss, in most instances, of sound teeth.

Heretofore, commercially available dentifrices containing abrasives such as insoluble sodium metaphosphate (NaPO$_3$) calcium hydrogen phosphate dihydrate-/anhydrous calcium hydrogen phosphate, (CaHPO$_4$.2H$_2$O/CaHPO$_4$), calcium pyrophosphate (Ca$_2$P$_2$O$_7$), and silica (SiO$_2$) have exhibited relatively unsatisfactory enamel-polishing qualities and consequently have not been wholly effective in preventing the reaccumulation of materia alba, oral debris, plaque, pellicle, exogenous stains, and dental calculus. In particular, while conventional cleaning and polishing agents used with a toothbrush are capable, to varying degrees, of removing materia alba, food particles, exogenous stains, and other tooth surface pigmentations when utilized in ordinary daily brushings, they have not exhibited the ability to remove the more resistant forms of enamel pigments and to produce a smooth tooth surface resistant to dental calculus reformation. Furthermore, these conventional abrasives leave the teeth esthetically less desirable than would more effective polishing agents.

In an attempt to improve enamel-polishing qualities and cleaning efficiency, some commercial dentifrices now contain abrasive materials, such as alumina (Al$_2$O$_3$), which have been reported to impart a high polish to dental enamel when a low particle size is employed (100 percent less than 0.5 microns in alpha alumina). However, such materials do not clean enamel effectively without excessively abrading the dental hard tissue (i.e., enamel and dentin).

The benficial effects, in terms of a reduction in the incidence of dental caries, resulting from the incorporation of water-soluble fluoride salts, such as sodium fluoride, are well known. However, efforts to utilize such salts in dentifrices suitable for home use have been handicapped by the tendency for fluoride ions to be deactivated and rendered unavailable by other ingredients, particularly the abrasive component of such dentifrices. While generally speaking, dentifrice abrasives in therapeutic products used today are to varying degrees compatible with fluoride agents, there is a wide variation in compatibility. Calcium-containing abrasives are not particularly compatible. While the non-calcium-containing abrasives are somewhat more compatible, they frequently are inferior with regard to enamel polishing.

For example, Cooley et al. U.S. Pat. No. 3,070,510 teaches the use of substantially water-impervious, cross-linked, thermosetting, highly-polymerized resins as dentifrice cleaning and polishing agents. Although resin agents of the type disclosed in the Cooley et al. patent exhibit improved fluoride ion compatibility relative calcium calcium pyrophosphate, these agents similarly do not provide satisfactory cleaning and polishing characteristics.

Saul et al. U.S. Pat. No. 3,105,013 recommends using calcined aluminum silicate as a dental abrasive on the basis of its compatibility with fluoride adjuvants. However, the preferred material of the Saul et al. patent, "Kaopolite SF", as commercially available is an off-white color and is thus esthetically undesirable in a commercial dentifrice.

Japanese Pat. No. 24224/74 describes dental abrasives combining calcined kaolins with other abrasives such as calcium carbonate, calcium hydrogen phosphate dihydrate, and the like. The Japanese patent teaches nothing concerning the purification of the kaolin, and it specifically states that the use of calcined kaolin alone as a dental abrasive is undesirable.

Thus, prior art materials intended for use as cleaning and polishing constituents of dentifrice preparations have been unsatisfactory in one or more of the following respects, namely, relatively poor cleaning and polishing performances (especially with respect to prevention of reaccumulation of dental calculus, pellicle, materia alba, and the more resistant forms of oral hard tissue stains and pigmentations), incompatibility with fluoride-containing anticariogenic agents, and adverse abrasion.

SUMMARY OF THE INVENTION

In accordance with the present invention, it has been found that new and more effective dentifrice preparations may be obtained by incorporating therein as cleaning and polishing constituents purified, calcined kaolin particles predominantly of the gamma alumina and/or mullite form, not more than a minor amount of titanium-containing and other impurities being present and the particles being at least predominantly less than about 10 microns in diameter. The purified, calcined kaolin of this invention exhibits a brightness of at least about 93.0 and has a whiteness index of not more than about 10.0 when measured in the manner described hereinafter in detail.

It has further been found that the novel cleaning and polishing agents of the present invention may be used with non-toxic amounts of water-soluble anticariogenic adjuvants such as sodium fluoride. It has likewise been discovered that application of the dentifrice preparations of the present invention to the teeth provides a novel method for cleaning and polishing teeth and for reducing the incidence of gingival disease.

Through the use of the cleaning and polishing agents of the present invention the difficulties experienced with prior art dentifrice cleaning and polishing agents may be overcome, and compositions of the present invention may therefore be used to formulate dentifrices with superior cleaning and polishing capabilities and with enhanced anticariogenic ion compatibilities.

Accordingly, it is a primary object of the present invention to provide a cleaning and polishing agent which is capable of reducing the reformation of dental calculus and the incidence of gingivitis and yet which is suitable for incorporation in a dentifrice preparation.

Another object of the present invention is to provide an anticalculus cleaning and polishing agent of the character described which is effective in removing pellicle and dental enamel stains and pigmentations.

Another object of the present invention is to provide anticalculus dentifrice preparations incorporating a cleaning and polishing agent of the character described.

A still further object is to provide a dentifrice preparation incorporating at least one fluoride-containing anticariogenic adjuvant in combination with an anticalculus cleaning and polishing agent of the character described which further serves to enhance the effectiveness of the anticariogenic adjuvant.

These and other objects, advantages, and features of the present invention will hereinafter appear, and, for purposes of illustration, but not of limitation, exemplary embodiments of the subject invention are hereinafter described in detail.

DESCRIPTION OF THE PREFERRED EMBODIMENTS

In accordance with the subject invention, it has been found that optimal cleaning and polishing characteristics for a dentifrice cleaning and polishing agent are exhibited by purified, calcined kaolin particles predominantly of the gamma alumina and/or mullite form, not more than a minor amount of titanium-containing and other impurities being present and the particles being at least predominantly less than about 10 microns in diameter.

Where the purified kaolin particles are highly calcined, a major proportion (i.e., at least about 75%, by weight) of the particles is preferably less than 2 microns in diameter, with a minor proportion (i.e., the balance) lying substantially in the range of about 2-10 microns.

Where the particles are less highly calcined, about 25-50%, by weight, of the purified kaolin particles lie between about 2 and 10 microns in diameter, up to about 15%, by weight, of the particles being greater than 10 microns in diameter and up to about 70%, by weight, of the particles being less than 2 microns in diameter.

The purified, calcined kaolin of this invention exhibits a brightness of at of about 93.0 and has a whiteness index of not more than about 10.0. Brightness as used herein is determined in accordance with TAPPI Test Method T 646 using a wave-length of 460 millimicrons. Whiteness index is a difference between the brightness readings at 400 and 700 millimicrons, with a lower whiteness index thus being more desirable.

In addition, it has been found that purified, calcined kaolins of the character described may be advantageously used with water-soluble fluoride-ion-containing anticariogenic adjuvants such as sodium fluoride.

As a result of the foregoing, the cleaning and polishing compositions of the present invention find utility in therapeutic dentifrices (i.e., dentifrices containing at least one anticariogenic ionic adjuvant in combination with a compatible cleaning and polishing agent and designed to reduce the incidence and severity of dental caries) or dentifrices which, although not containing fluorides or other anticariogenic agents, nonetheless have therapeutic utility in reducing gingival disease.

CLEANING AND POLISHING AGENTS

The purified, calcined kaolin abrasives of this invention may be obtained by calcining (i.e., heat treating) kaolinite, $[Al_4Si_4O_{10}(OH)_8]$, which has been mined, cleaned, dried, and fractionated. Prior to calcining, the material is subjected to a purification procedure, such as the flocculation and related steps described in U.S. Pat. No. 3,477,809, in order to remove titanium-containing impurities and ultrafine particles.

The purified material is calcined at a temperature lying in the range of about 950° C. to 1150° C. If the temperature does not reach 950° C., the purified kaolinite remains predominantly meta-kaolin, a material which is insufficiently hard to clean and polish satisfactorily from a dental standpoint. Material which has been calcined at about 950° C. is predominantly gamma alumina generally taking the form of spinel-type crystals. However, if the purified material is more highly calcined, (i.e., is subjected to temperatures of up to about 1150° C.), the gamma alumina undergoes a change to highly crystalline mullite $(3Al_2O_3 \cdot 2SiO_2)$, generally taking the form of small, needle-like crystals. If the materials are overcalcined (i.e., subjected to temperatures of about 1250° C. or more), larger mullite crystals and materials such as cristobolite $(SiO_2)$ are formed. Material containing large amounts of cristobolite and large mullite crystals are unsatisfactory from a dental standpoint because of their tendency to scratch the tooth enamel unless reduced in size by milling or grinding. As a consequence, the purified, calcined kaolins of this invention are predominantly of the gamma alumina and/or mullite form.

After calcining, in which the material agglomerates into large masses, grinding and/or milling must be used to obtain an abrasive having a particle size distribution lying in the range found to be useful in dentifrice preparations.

When lower calcining temperatures are employed (i.e., in the range of about 950° C. to 1050° C.), more economical dry grinding processes such as conventional Bauer-milling, may be employed. However, where higher calcining temperatures of 1050° C. and especially about 1150° C. are employed, it has been found that the relatively greater amounts of hard crystalline material formed at these temperatures may most conveniently be treated by using known wet sand grinding procedures. Sand grinding techniques may be employed with all of the abrasives of this invention although, as noted, for reasons of economy, it is preferred to use Bauer-milling treatments for materials calcined in the lower temperature ranges. Bauer-milling procedures may be employed with materials calcined in the range of about 1150° C., but it is preferred to use sand grinding techniques with these materials.

Where Bauer-milling procedures are employed, the abrasives may advantageously comprise up to about 15%, by weight, particles greater than 10 microns in diameter. Preferably, about 10–15% of the particles are greater than 10 microns in diameter. Up to 70%, by weight, of the particles may be less than 2 microns in diameter. Advantageously, ultrafine particles (i.e., particles 0.5 in diameter) are excluded.

Where said grinding techniques are used with the harder, more highly calcined materials treated in the range of about 1150° C., the particles are ground much finer than where Bauer-milling is employed. Such sand ground materials are preponderantly less than 1 micron in diameter, and at least 75%, preferably about 90% or more, are less than 2 microns in diameter. Such sand ground materials should not contain significant numbers of particles over 10 microns in diameter.

Exemplary abrasives in accordance with this invention are set forth in the following examples. The specified degree of calcination (relatively high or relatively low) may be obtained by altering the feed rate of material to the calciner, by varying the calcination residence time of the thickness of the material bed in the calciner, or by other methods known in the art.

EXAMPLE I

A purified kaolin calcined at 1050° C. in a laboratory furnace and ground by hand.

EXAMPLE II

A purified kaolin calcined at 950° C. in a pilot plant with a relatively low degree of calcination and subsequently Bauer-milled.

EXAMPLE III

A purified kaolin calcined in a pilot plant at 950° C. with a relatively high degree of calcination and subsequently Bauer-milled.

EXAMPLE IV

A purified kaolin calcined in a pilot plant at 1050° C. with a relatively low degree of calcination and subsequently Bauer-milled.

EXAMPLE V

A purified kaolin calcined in a pilot plant at 1150° C. with a relatively high degree of calcination and subsequently Bauer-milled.

EXAMPLE VI

A purified kaolin calcined at 1150° C in a pilot plant with a relatively high degree of calcination and subsequently sand ground.

EXAMPLE VII

A purified kaolin production calcined at a temperature in the range of approximately 1000°–1050° C. with a relatively high degree of calcination and subsequently Bauer-milled.

Particle size distributions for the abrasives of the foregoing Examples, as determined by the Centrifugal-Casagrande-Hydrometer method, are given in the following Table.

TABLE I

| Abrasive | Particle Size Range Weight % | | |
|---|---|---|---|
| | 2 | 2–10 | 10 |
| Example I | 62 | 31 | 7 |
| Example II | 54 | 35 | 10 |
| Example III | 56 | 34 | 10 |
| Example IV | 60 | 28 | 12 |
| Example V | 46 | 41 | 13 |
| Example VI | 90 | 10 | 0 |
| Example VII | 70 | 24 | 6 |

The abrasives of this invention have also been characterized by x-ray diffraction procedures using a De Bye-Sherrer 11.46 cm powder camera. The results of these x-ray analyses are reported in Table II as the number of x-ray lines characteristic of the presence of a given material and thus provide a rough quantitative indication of the amounts of the respective constituents.

TABLE II

| Abrasive | X-ray Data (Number of Lines) | |
|---|---|---|
| | Gamma Alumina | Mullite |
| Example I | 5 | 0 |
| Example II | 3 | 0 |
| Example III | 4 | 11 |
| Example IV | 3 | 6 |
| Example V | 0 | 17 |
| EXample VI | 0 | 17 |
| Example VII* | 3–4 | 6–11 |

*Data for Example VII varies due to variations in material that occur in production scale runs and are presented as ranges.

Elemental analysis of the purified, calcined kaolins of this invention by arc spectrometry techniques shows that the major constituents (i.e., constituents accounting for more than 5% by weight) of the treated material are aluminum and silicon. (The other major constituent, oxygen, as is known, cannot be analyzed by the arc spectrometry technique.) These data plus the other minor and trace constituents are given in Table III.

TABLE III

| Rac Spectrometric Elemental Analysis of Purified, Calcined Kaolins | |
|---|---|
| Major Constituents (5%, by weight) | Al Si |
| Minor Constituents (0.01–5.0%, by weight) | Cr Fe Mg Na Ni Ti V Zr |
| Trace Constituents (0.01%, by weight) | Cu Mn Ca |

The purified, calcined kaolin materials of the invention thus contain not more than a minor amount of titanium-containing and other impurities, with the particles being predominantly of the gamma alumina and/or mullite form, and at least predominantly less than about 10 microns in diameter.

I. DENTIFRICE PREPARATIONS

The purified, calcined kaolin cleaning and polishing agents of the present invention are employed in dentifrice preparations within the range of about 10 up to about 95%, by weight, depending upon the particular formulation desired, as is well known to one skilled in the art.

Toothpastes preferably contain a total of about 20–70% cleaning and polishing agent, by weight, whereas tooth powders contain about 60–90% cleaning and polishing agent, by weight. Liquid dentifrices typically employ about 10–40%, by weight, abrasive, whereas gel type dentifrices utilize about 20–40% abrasive, by weight.

Where desired, a portion (i.e., up to 75%, by weight, of the abrasive constituents) of the purified calcined kaolins of this invention may be replaced by fillers, extenders or other abrasives such as talcs, aluminum silicates, zirconium silicate ($ZrSiO_4$), calcium pyrophosphate ($Ca_2P_2O_7$), calcium hydrogen phosphate dihydrate/anhydrous calcium hydrogen phosphate ($CaHPO_4 \cdot 2H_2O/CaHPO_4$), insoluble sodium metaphosphate ($(NaPO_3)x$), calcium carbonate ($CaCO_3$), silicas ($SiO_2$), and substantially water-impervious, cross-linked, thermosetting, highly-polymerized synthetic resins (e.g., melamine formaldehyde resins, such as those described in U.S. Pat. Nos. 3,070,510, and 3,251,800), and mixtures of these other agents as well as other dental abrasive materials. An especially preferred material that may be mixed with the abrasives of this invention is uncalcined, purified kaolin of the same type.

Dentifrice preparations utilizing the cleaning and polishing agents of the subject invention are prepared in a conventional manner and usually include additional ingredients which render the overall composition commercially acceptable to consumers.

Thus, toothpastes require a binder substance to impart desired textural properties. Natural gum binders such as gum tragancanth, gum karaya, gum arabic, etc., and seaweed derivatives such as Irish moss and alginates, and water-soluble cellulose derivatives, such as sodium carboxymethyl cellulose can be used for this purpose. Synthetic colloidal magnesium silicate, such as "Laponite", also may be used and is preferred in gel-type formulations. Desirably, those materials are employed which are most compatible with fluoride ion. Improvements in texture can also be attained by including an additional material such as colloidal magnesium aluminum silicate, fumed silica, or the like. Binders in an amount of from 0.5% to 5.0%, by weight, can be used to form a satisfactory toothpaste.

Toothpastes conventionally contain sudsing agents. Suitable sudsing agents include, but are not limited to, water-soluble alkyl sulfates having from 8 to 18 carbon atoms in the alkyl radical, such as sodium lauryl sulfate, water-soluble salts of sulfonated monoglycerides of fatty acids having from 10 to 18 carbon atoms in the alkyl radical such as sodium coconut monoglyceride sulfonate, salts of fatty acid amides of taurines such as sodium-N-methyl palmitoyl taurine, and salts of fatty acid esters of isethionic acid. Sudsing agents can be used in the compositions of this invention in an amount of from about 0.5% to about 5.0%, by weight, of the total composition.

It is also desirable to include some humectant material in a toothpaste to keep it from hardening. Materials commonly used for this purpose include glycerine, sorbitol, and other polyhydric alcohols. The humectants can comprise up to 35% of conventional toothpaste compositions. In the case of gel-type formulations, humectants may be used at levels as high as 80%, by weight.

Finally, flavoring materials may be included in a toothpaste formulation including small amounts of oils of wintergreen and peppermint and sweetening agents such as saccharin, dextrose, and levulose.

The non-fluoride dentifrices of this invention generally are employed at their natural pH values which lie in the range of about 6.0–8.0, although, if desired, the pH may be adjusted in the range of about 4.0–9.0 with acetic acid/sodium hydroxide, various sodium phosphates or other buffering agents.

Compositions of exemplary dentifrice preparations employing the cleaning and polishing agents of the present invention are given in the following Examples.

EXAMPLE VIII

| Constituent | Parts by Weight |
|---|---|
| Purified, calcined kaolin (Ex. I) | 40.0 |
| Water | 27.0 |
| Glycerin | 15.0 |
| Sorbitol (70% aqueous solution) | 10.0 |
| Sodium coconut monoglyceride sulfonate | 1.0 |
| Sodium lauryl sulfate | 1.0 |
| Veegum (Magnesium aluminum silicate) | 0.5 |
| Sodium carboxymethyl cellulose | 1.0 |
| Flavoring agents | 1.5 |
| Trisodium citrate | 1.0 |
| Propyl p-hydroxybenzoate | 0.1 |
| Methyl p-hydroxybenzoate | 0.2 |
| Miscellaneous (color, sweetener, etc.) | <2.0 |

EXAMPLE IX

| Constituent | Parts by Weight |
|---|---|
| Purified, calcined kaolin (Ex. VII) | 39.0 |
| Water | 26.0 |
| Glycerin | 12.0 |
| Sorbitol (70% aqueous solution) | 15.0 |
| Sodium lauryl sulfate | 2.0 |
| Veegum (Magnesium aluminum silicate) | 0.8 |
| Sodium carboxymethyl cellulose | 1.5 |
| Flavoring agents | 1.0 |
| Trisodium citrate | 0.8 |
| Propyl p-hydroxybenzoate | 0.1 |
| Methyl p-hydroxybenzoate | 0.2 |
| Miscellaneous (color, sweetener, etc.) | <2.0 |

EXAMPLE X

| Constituent | Parts by Weight |
|---|---|
| Purified, calcined kaolin (Ex. VI) | 45.0 |
| Water | 20.0 |
| Glycerin | 12.0 |
| Sorbitol (70% aqueous solution) | 15.0 |
| Sodium coconut monoglyceride sulfonate | 1.0 |
| Sodium lauryl sulfate | 1.0 |
| Veegum (Magnesium aluminum silicate) | 0.6 |
| Sodium carboxymethyl cellulose | 1.5 |
| Flavoring agents | 2.0 |
| Trisodium citrate | 0.3 |
| Propyl p-hydroxybenzoate | 0.1 |
| Methyl p-hydroxybenzoate | 0.2 |
| Miscellaneous (color, sweetener, etc.) | 2.0 |

EXAMPLE XI

| Constituent | Parts by Weight |
| --- | --- |
| Purified, calcined kaolin (Ex. IV) | 25.0 |
| Purified Kaolin (uncalcined) | 15.0 |
| Water | 26.0 |
| Glycerin | 15.0 |
| Sorbitol (70% aqueous solution) | 10.0 |
| Sodium lauryl sulfate | 2.0 |
| Veegum (Magnesium aluminum silicate) | 1.0 |
| Sodium carboxymethyl cellulose | 1.0 |
| Flavoring agents | 1.5 |
| Propyl p-hydroxybenzoate | 0.1 |
| Methyl p-hydroxybenzoate | 0.2 |
| Miscellaneous (color, sweeteners, buffers, etc.) | 3.0 |

The formulation of a suitable gel type dentifrice is given in Examples XII and an exemplary toothpowder is set forth in Example XIII.

EXAMPLE XII

| Constituent | Parts by Weight |
| --- | --- |
| Purified calcined kaolin (Ex. III) | 37.0 |
| Sorbitol, 70% solution | 17.50 |
| Laponite (magnesium silicate) | 1.05 |
| Sodium carboxymethyl cellulose | 0.2 |
| Glycerin | 14.0 |
| Sodium lauryl sulfate | 1.5 |
| Flavoring Agents | 1.0 |
| Miscellaneous (sweetener, preservative, etc.) | 3.0 |
| Water | 25.0 |

EXAMPLE XIII

| Constituent | Parts by Weight |
| --- | --- |
| Purified calcined kaolin (Example II) | 80 |
| Detergent | 2 |
| Flavoring and sweetener | 1 |
| Filler | 17 |

As previously indicated, the cleaning and polishing agents of the present invention also function as compatible carriers for anticariogenically-effective and non-toxic amounts of water-soluble fluoride-containing anticariogenic adjuvants in anticariogenic dentifrice preparations. Preferably, the adjuvant is present in the form of water-soluble fluoride-containing compounds capable of supplying fluoride. The preferred adjuvant is sodium fluoride, NaF, although other materials such as stannous fluorozirconate ($SnZrF_6$), indium fluorozirconate ($InZrF_7$), stannous fluoride ($SnF_2$), and complex zirconium-germanium fluorides [e.g., $Zr(GeF_6)_2$, $ZrGeF_8$, $Ge(ZrF_6)_2$, and $ZrOGeF_6$] may be employed. Sodium fluoride is preferred by virtue of the absence of objectionable taste, lack of enamel pigmentation, and the freedom from damage to gingival tissue, and by reason of anticariogenic effectiveness obtainable therewith.

Other suitable adjuvants include water-soluble fluoride salts such as $SnF_4$, KF, $InF_3$, $PbF_2$, $FeF_2$, $NH_4F$, and LiF, as well as more complex water-soluble fluoride-containing adjuvants such as fluorosilicates, e.g., $Na_2SiF_6$, other fluorozirconates, e.g., $CaZrF_6$, $Na_2ZrF_6$, $K_2ZrF_6$, fluorostannites, e.g., $NaSnF_3$, fluoroborates, e.g., $NaBF_4$, fluorotitanates, e.g., $NaTiF_5$, other fluorogermanates, e.g., $K\ GeF_6$, and mixed halides, e.g., SnClF and $Sn_2ClF_3$. Mixtures of suitable adjuvants may also be utilized. Another suitable adjuvant comprises a mixture of a fluoride salt and an active phosphate compound such as Victamide as set forth and described in U.S. Pat. No. 3,666,855, issued May 30, 1972.

In general, an anticariogenic dentifrice preparation produced in accordance with the subject invention will contain from about 0.05 up to 1.0%, by weight, of the dentifrice preparation of the fluoride-containing anticariogenic adjuvant so as to desirably provide about 1000 ppm fluoride ion. Sodium fluoride is preferably provided at a level of 0.22%, by weight, and when $SnF_2$ is utilized, the desired amount is preferably about 0.4%.

Preferably, such fluoride-containing dentifrice preparations are employed in their natural pH ranges (i.e., about 8.5 to 9.5), although, if desired, the pH range may be adjusted to about 4.0 to 9.0 with acid/sodium hydroxide or various sodium phosphates, or other buffering agents.

Exemplary formulations of fluoride-containing dentifrices in accordance with this invention are given in the following examples.

EXAMPLE XIV

| Constitutent | Parts by Weight |
| --- | --- |
| Purified, calcined kaolin (Ex. VII) | 40 |
| Water | 27 |
| Sodium carboxymethyl cellulose | 1 |
| Veegum (Magnesium aluminum silicate) | .5 |
| Sorbitol | 10 |
| Glycerin | 15 |
| Sodium lauryl sulfate | 1.5 |
| Trisodium citrate | 2 |
| Sodium fluoride | .22 |
| Flavorings, colorings, preservatives, etc. | 3 |

EXAMPLE XV

| Constituent | Parts by Weight |
| --- | --- |
| Purified, calcined kaolin (Ex. VI) | 44 |
| Water | 22 |
| Sodium carboxymethyl cellulose | 1 |
| Veegum (Magnesium aluminum silicate) | .7 |
| Sorbitol | 10 |
| Glycerin | 15 |
| Sodium lauryl sulfate | 2.0 |
| Stannous Fluoride | 0.4 |
| Flavorings, colorings, preservatives, etc. | 3 |

EXPERIMENTAL EVALUATIONS

The superiority of the purified, calcined kaolin cleaning and polishing compositions disclosed herein has been substantiated by the following experimental evaluations.

Enamel polishing data are obtained with moist bovine teeth that are ground and trimmed to the appropriate size in order to fit into an acrylic resin mold and embedded in Wood's metal. After cooling, the teeth are leveled with care being taken in order to insure that the leveled area does not cut into the dentin and is parallel to the base. The teeth are of sufficient size to provide an area 0.7 to 1.1 cm. without endangering the accuracy of the method. The teeth are dulled with 600 grit silicon carbide, followed by a very complete and thorough rinsing with distilled water. The teeth are then placed on the stage of a V-8 cross-brushing machine. They are then brushed a predetermined number of strokes with the material to be tested. The teeth are thoroughly rinsed with distilled water upon completion of the run and blotted dry with a soft cloth towel.

The reflectance of the polished tooth surface is determined by means of a reflectometer especially adapted to detect the changes in the degree of polish of the enamel surface. The reflectometer is constructed so that the enamel is exposed to a beam of light, and the amount of light reflected from the enamel surface is determined by a photoelectric cell which in turn activates a strip chart recorder. The smoother the enamel surface, the smaller the amount of diffused and absorbed light and, hence, the higher the reflectance reading. The reflectometer scale is set so that 0% is total darkness and 100% is white carrara glass, and data for the abrasives tested hereinafter are reported on this scale.

The harmfulness of a dental abrasive can be expressed in terms of dentin and enamel abrasion values. Dentin abrasion values for dentifrice cleaning and polishing agents may be determined by separating the dentin from the enamel portions of human teeth and exposing them to neutron radiation whereby a portion of phosphate content is converted to $P_{32}$. Each dentin or enamel portion is mounted in a low melting alloy, such as Wood's metal, and is submerged in a slurry of the cleaning and polishing agent to be tested. An automatic toothbrush is arranged so that it can be moved back and forth across the surface of the submerged portion of the specimen and the pressure of this toothbrush is adjusted to a standard level. The specimen is subjected to brushing action for a given number of strokes, and removed from the slurry. The radioactivity of the slurry is then determined by conventional means.

A similar procedure is used for enamel abrasion. Human enamel may be used, but bovine enamel is more easily obtained and thus is more frequently used.

An equivalent piece of dentin or enamel, irradiated concurrently with the dentin or enamel portion of be brushed, is weighed, dissolved in hydrochloric acid, and the radioactivity determined. Using this reference, a correction for self-adsorption by the dentifrice is made.

A standard slurry for measuring dentin abrasion is made from calcium pyrophosphate ($Ca_2P_2O_7$). The concentration of the standard slurry is 25.0 grams per 50 cc. of a one percent aqueous sodium carboxymethyl cellulose solution.

To determine the abrasion value of a cleaning and polishing agent, a portion of irradiated tooth dentin or enamel is first brushed with a standard calcium pyrophosphate slurry. The same portion specimen the specimen is then cleaned with water and brushed with a slurry of a cleaning and polishing agent to be tested. The specimen is again cleaned and brushed with the standard calcium pyrophosphate slurry. Each of these slurries is counted, the average amounts of radioactive dentin or enamel removed by the brushing with the slurries of standard calcium pyrophosphate and with the cleaning and polishing agent being tested are calculated. The amount of dentin or enamel removed by the standard calcium pyrophosphate slurry is normally given an arbitrary value of 475. A ratio of the experimental reading to the standard calcium pyrophosphate is calculated in order to obtain the sought-for experimental abrasion value.

The effectiveness of a dental abrasive as a compatible carrier vehicle for fluoride-containing adjuvants may be determined by obtaining the amounts of available fluoride ion in solution. Percentage availability refers to a comparison of an ionic concentration level for a reference solution of the adjuvant without the carrier vehicle (e.g., an aqueous solution of the adjuvant maintained at a reference ionic concentration level, such as 1,000 ppm fluoride). A percentage ratio of the ionic concentration level for the combination solution relative to the reference solution is determined by conventional techniques. Thus, a combination solution of carrier vehicle and sodium fluoride which analyzes 900 ppm fluoride concentration compared to a reference solution of sodium fluoride at 1,000 ppm fluoride exhibits a 90% availability insofar as ability to provide fluoride ions is concerned.

Enamel polishing, enamel and dentin abrasion data, and fluoride availability data were obtained for a number of dentifrice abrasives in accordance with this invention. For comparative purposes, the same data were obtained for an unpurified, calcined aluminum silicate abrasive.

These data are reported in TABLE IV.

TABLE IV

| Abrasive | Enamel Polish (4000 Strokes) | Abrasion Data | | Flouride Percent Availability |
| --- | --- | --- | --- | --- |
| | | Dentine | Enamel | |
| Example I | 99 | 245 | 596 | 70.6 |
| Example II | 99 | 368 | 501 | 69.8 |
| Example III | 100 | 393 | 531 | 67.6 |
| Example IV | 99 | 335 | 509 | 66.2 |
| Example IV | 99 | 658 | 738 | 82.4 |
| Example VI | 101 | 347 | 475 | 72.5 |
| Example VII | 102 | 456 | 746 | 72.2 |
| Unpurified, calcined aluminum silicate* | 96 | 434 | 811 | 56.0 |

*Such an unpurified, calcined aluminum silicate is taught in U.S. Pat. No. 3,105,013, and may be commercially obtained from Kaopolite, Inc., Elizabeth N.J., under the trade name "Kaopolite-SF". This material differs from the materials of this invention in that it contains neither the minor proportion of particles greater than 10 microns nor the requisite amount between 2 and 10 microns as required for the Bauer-milled abrasives of this invention; in that it appears to be significantly more crystalline and unduly abrasive; and in that it is off-white in color rather than pure white and thus produces darker, less attractive, tan dentifrices such that it is highly undesirable for use in dentifrices.

Brightness measurements were determined for exemplary material in accordance with this invention (Example 7) and for an unpurified, calcined aluminum silicate available under the trademark "Kaopolite-SF" using TAPPI Test Method T-646, a GE Recording Specrophotometer, and a wave length of 460 millimicrons. Readings were also taken at wave lengths of 400 and 700 millimicrons in order to obtain a brightness index for these materials. These data are reported in Table V.

TABLE V

| Abrasive | Brightness | Whiteness Index |
| --- | --- | --- |
| Example VII | 94.5 | 9.6 |
| Unpurified, calcined aluminum silicate | 91.5 | 12.5 |

Brightness The foregoing data are supported of the accordance dental health advance that may be achieved by utilizing dentifrice preparations calcined the aluminum calcined kaolin dental cleaning and Kaopolite-SF"agents of this invention. In addition, regular use of the Recording permits and reduction in the incidence and severity of gingival disease to be achieved. order index

We claim:

1. A method for reducing the incidence of enamel abrasion and gingival disease with increased fluoride availability comprising the application to the teeth of a fluoride-containing dentifrice preparation comprising a cleaning and polishing agent consisting essentially of purified, calcined kaolin particles predominantly of the gamma alumina or mullite form, not more than a minor amount of titanium-containing and other impurities being present and the particles being at least predominantly less than about 10 microns in diameter, a major proportion of the particles being less than 2 microns in diameter and a minor proportion lying in the range of about 2–10 microns, said agent having a brightness of at least about 93.0 and a whiteness index of not more than about 10.0.

2. A method, as claimed in claim 1, wherein the fluoride is sodium fluoride.

3. A method as claimed in claim 1, wherein the fluoride is present at a level of about 0.05–1.0% by weight, of the dentifrice preparation.

4. A method, as claimed in claim 1, wherein at least about 75%, by weight, of the particles are less than about 2 microns in diameter, with the balance lying substantially in the range of about 2–10 microns.

5. A method, as claimed in claim 1, wherein about 25–50%, by weight, of the purified kaolin particles lie in the range of about 2–10 microns, up to about 15%, by weight, of the particles being greater than 10 microns in diameter and up to about 70%, by weight, of the particles being less than 2 microns in diameter.

6. A dentifrice preparation having reduced enamel abrasion and increased fluoride availability comprising a water-soluble fluoride containing anticariogenic adjuvant and a cleaning and polishing agent consisting essentially of purified, calcined kaolin particles, predominantly of the gamma alumina or mullite form, not more than a minor amount of titanium-containing and other impurities being present and the particles being at least predominantly less than about 10 microns in diameter, a major proportion of the particles being less than 2 microns in diameter and a minor proportion lying in the range of about 2–10 microns, said agent having a brightness of at least about 93.0 and a whiteness index of not more than 10.0.

7. A dentifrice preparation, as claimed in claim 6, wherein the adjuvant is sodium fluoride.

8. A dentifrice preparation, as claimed in claim 6, wherein the anticariogenic adjuvant is present at a level of about 0.05 – 1.0%, by weight, of the preparation.

9. A dentifrice preparation, as claimed in claim 7, wherein the cleaning and polishing agent is present at a level of about 20–95%, by weight, of the dentifrice preparation.

10. A dentifrice preparation, as claimed in claim 7, wherein at least about 75%, by weight, of the particles are less than about 2 microns in diameter, with the balance lying substantially in the range of about 2–10 microns.

11. A dentifrice preparation, as claimed in claim 7, wherein about 25–50%, by weight, of the purified kaolin particles lie in the range of about 2–10 microns, up to about 15%, by weight, of the particles being greater than 10 microns in diameter and up to about 70%, by weight, of the particles being less than 2 microns in diameter.

* * * * *

UNITED STATES PATENT AND TRADEMARK OFFICE
CERTIFICATE OF CORRECTION

PATENT NO. : 4,122,163
DATED : October 24, 1978
INVENTOR(S) : Joseph C. Muhler, et al.

It is certified that error appears in the above-identified patent and that said Letters Patent are hereby corrected as shown below:

Column 1, line 24 - "anticariogenicadjuvants" should be --anticariogenic adjuvants --;

Column 2, line 27 - "calcium calcium" should be -- to calcium--;

Column 3, line 64 - "of"(second occurance)should be -- least --;

Column 13, lines 1-8 should read as follows:

-- The foregoing data are supportive of the significant
dental health advance that may be achieved by utilizing
dentifrice preparations containing the purified calcined
kaolin dental cleaning and polishing agents of this
invention. In addition, regular use of the preparation
permits significant reduction in the incidence and severity
of gingival disease to be achieved.--

Signed and Sealed this

Thirtieth Day of January 1979

[SEAL]

Attest:

RUTH C. MASON
Attesting Officer

DONALD W. BANNER
Commissioner of Patents and Trademarks